US00PP08134P

United States Patent [19]

Holtkamp, Sr.

[11] Patent Number: Plant 8,134

[45] Date of Patent: Feb. 9, 1993

[54] AFRICAN VIOLET PLANT NAMED HELSINKI

[76] Inventor: Reinhold Holtkamp, Sr., Blumenstrasse 28, D 4242 Rees-Haffen, Fed. Rep. of Germany

[21] Appl. No.: 736,612

[22] Filed: Jul. 26, 1991

[51] Int. Cl.[5] ..... A01H 5/00

[52] U.S. Cl. ..... Plt./69.1

[58] Field of Search ..... Plt./69.1, 69.2

*Primary Examiner*—James R. Feyrer

*Attorney, Agent, or Firm*—Foley & Lardner

[57] ABSTRACT

A new and distinct cultivar of African violet named Helsinki characterized by its extra large growth habit (35–45 cm in diameter); two-tone pink, semi-double to double flowers with slightly wavy edges; strong stems which curve toward the center to form a bouquet above the leaves; profuse flowering; large, dark green, oval to spear-shaped leaves; flowering 12–13 weeks after planting of unrooted shoot, and by its long lasting and non-dropping flowers.

1 Drawing Sheet

The present invention comprises a new and distinct cultivar of African violet plant, botanically known as *Saintpaulia ionantha*, and hereinafter referred to by the cultivar name Helsinki.

The new cultivar was referred to during the breeding and selection process by the designation 906/70 gross apfl.d.bl. and is a product of a planned breeding program. The cultivar was originated from a cross made by me in the controlled breeding program in Haffen, Federal Republic of Germany. The female, or seed parent, was a cultivar designated Arizona/6/III. The male, or pollen parent, was a cultivar designated 287 rot rosa w.

Helsinki was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Helsinki has not been observed under all possible environmental conditions. The phenotype may vary significantly with variations in environment such as temperature, light intensity and day length. The following observations, measurements and values describe the new cultivar as grown in a 15 cm pot in Haffen, West Germany and Nashville, Tenn., under greenhouse conditions which closely approximate those generally used in commerical practice.

The following traits have been repeatedly observed and are determined to be basic characteristics of Helsinki, which in combination distinguish this African violet as a new and distinct cultivar:

1) Helsinki will grow as large as 35–45 cm in diameter.

2) Semi-double to double, two-tone pink flowers.

3) Strong, wirelike and upright flower stems curving toward the center.

4) First flash of flowers forms a bouquet above the leaves.

5) Profuse flowering.

6) Each plant carries 12–14 and more upright flower stems each of which carries 12–15 and more flowers.

7) Long lasting, non-dropping flowers.

8) Plant saleable 12 to 13 weeks after planting of unrooted shoot.

9) Seed capsules push slightly through.

10) Large, dark green, oval to spear-shaped leaves.

11) After maturity the flowers dry off, and remain on the peduncle without becoming infected by botrytis.

The accompanying color photographic drawing shows a typical specimen plant of the new cultivar grown in a 15 cm pot. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn.

Botanical Classification: *Saintpaulia ionantha*, Ramat., c.v. Helsinki.

Parentage:

*Male parent.*—287 rot rosa w.

*Female parent.*—Arizona/6/III.

Propagation: The new cultivar holds its distinguishing characteristics through successive propagations by leaf cuttings.

Plant: From 10 cm to 13 cm tall when grown in pots, and 35–45 cm in diameter when fully grown.

*Leaves.*—General form: Oval to spear-shaped. Diameter: 80–90 mm wide and 90–105 mm long. Texture: Leatherlike. Aspect: Hairy, shiny, slightly serrated. Veins: Upperside: visible; underside: well pronounced, light green to purplish green, shiny. Color (upperside): Yellow-green group 147 A and darker. Color (underside): Greyed-green group 194 C and Greyed-Purple Group 186 A to B. Petiole: Strong, purplish brown, hairy.

*Flowers.*—Buds: Size: 8–10 mm just before opening. Shape: Bell-shaped. Color: Pinkish green. Sepals: Five (5). Color: Purplish brown. Calyx: Shape: Flat. Aspect: Spear-shaped, hairy. Peduncle: Character: Strong upright, hairy. Color: Purplish brown. Individual flowers: Size: 43–48 mm. Shape: Semi-double to double with slightly wavy edges. Color (upperside): Large petals are red-purple group 65 C to D and lighter; center and small petals are red-purple Group 74 B to C. Under cooler temperatures and more intensive lighting, the two shades of pink tend to intensify. Color (underside): Large petals are red-purple group 65 C to D and lighter; small petals are red-purple group 74 D. Borne: Each flower stem carries 12–15 and more flowers on strong, upright peduncles that are free standing above the leaves, thereby forming a bouquet. Flowering habit: Flowers 12–13 weeks after planting an unrooted plantlet.

*Reproductive organs.*—Stamens: Two (2). Anthers: 2 composed of 4 anther cells, seed capsule pushes slightly through. Filaments: Yellowish green, 3–4 mm long. Styles: 5–7 mm long, pink, base of ovary light green and hairy.

*Roots.*—Normally developed, white when young, turning slightly brownish when older.

Disease Resistance: Up to date, Helsinki has shown very good resistance to all major violet diseases.

General Observations: Helsinki is a very attractive cultivar due to its extra large growth habit. It is designed to be grown in a 15 cm pot (instead of the regular 10 cm pot) and will grow as large as 35–45 cm in diameter. (The diameter can vary depending on how firmly the potting medium is compressed). A nice bouquet of flowers free standing above the leaves develops 12–13 weeks after planting an unrooted plantlet. Each of the 8–10 and more strong flower stems carries 12–15 and more semi-double to double flowers with slightly wavy edges. The flowers are two-tone pink: the darker pink color in the center radiates into the two small petals and all the small petals laying on top of them. The flowers are long-lasting and non-dropping. The bouquet is surrounded by large, dark green, oval to spear-shaped leaves.

I claim:

1. A new and distinct cultivar of African violet named Helsinki, as described and illustrated, and particularly characterized by its extra large growth habit (35–45 cm in diameter); two-tone pink, semi-double to double flowers with slightly wavy edges; strong stems which curve toward the center to form a bouquet above the leaves; profuse flowering; large, dark green, oval to spear-shaped leaves; flowering 12–13 weeks after planting of unrooted shoot, and by its long lasting and non-dropping flowers.

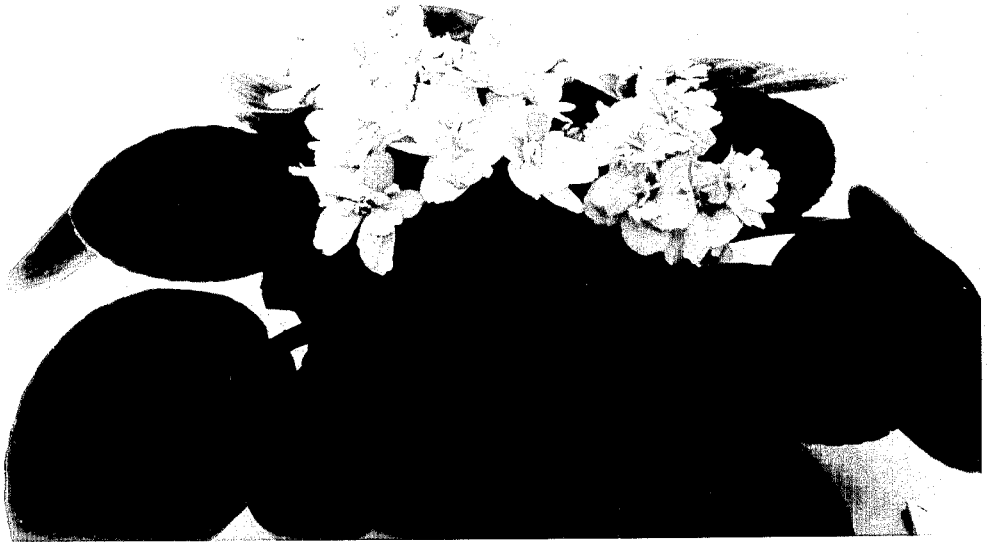

* * * * *